(12) United States Patent
Mancel et al.

(10) Patent No.: US 7,594,593 B2
(45) Date of Patent: Sep. 29, 2009

(54) APPARATUS FOR SPRAY APPLICATION OF A SUNLESS TANNING PRODUCT

(76) Inventors: Jim Mancel, 35 Kingsbridge Garden Circle, Mississauga, Ontario (CA) L5R 3Z5; John Marmora, 107 Carrington Drive, Richmond Hill, Ontario (CA) L4C 7X8

( * ) Notice: Subject to any disclaimer, the term of this patent is extended or adjusted under 35 U.S.C. 154(b) by 488 days.

(21) Appl. No.: 11/334,187

(22) Filed: Jan. 17, 2006

(65) Prior Publication Data

US 2006/0157499 A1 Jul. 20, 2006

(51) Int. Cl.
*B67D 5/52* (2006.01)
*A62C 2/08* (2006.01)
*A45D 44/00* (2006.01)

(52) U.S. Cl. .................. 222/135; 222/402.15; 222/94; 239/548; 239/566

(58) Field of Classification Search ............ 222/94, 222/129, 135, 136, 402.1, 402.14, 402.15, 222/402.23; 239/337, 548, 578, 549, 566; 132/333, 200
See application file for complete search history.

(56) References Cited

U.S. PATENT DOCUMENTS

| | | | |
|---|---|---|---|
| 2,720,422 A * | 10/1955 | Mercur | 222/174 |
| 2,868,421 A * | 1/1959 | Schott | 222/473 |
| 3,303,970 A * | 2/1967 | Breslau et al. | 222/134 |
| 3,506,159 A * | 4/1970 | Muller | 222/135 |
| 3,575,319 A * | 4/1971 | Safianoff | 222/135 |
| 3,677,441 A * | 7/1972 | Nixon et al. | 222/63 |
| 4,098,436 A * | 7/1978 | Kohlbeck | 222/182 |
| 4,401,240 A * | 8/1983 | Brack | 222/323 |
| 4,579,258 A * | 4/1986 | Brown et al. | 222/323 |
| 4,660,745 A * | 4/1987 | Hess, Jr. | 222/174 |
| 5,005,736 A * | 4/1991 | Portas | 222/135 |
| 5,971,209 A * | 10/1999 | Bayless | 222/135 |
| 6,966,461 B2 * | 11/2005 | Warner et al. | 222/174 |
| 7,048,151 B1 * | 5/2006 | Wertz et al. | 222/174 |
| 7,299,950 B2 * | 11/2007 | Laveault et al. | 222/174 |

* cited by examiner

*Primary Examiner*—Kevin P Shaver
*Assistant Examiner*—Stephanie E Tyler
(74) *Attorney, Agent, or Firm*—Robert M. Downey, PA

(57) ABSTRACT

An apparatus has a vertical tower that holds a plurality of containers in spaced vertical alignment. A control knob is connected to a cam mechanism which, upon rotation thereof, serves to move a linkage to operate actuator levers between an OFF position and an ON position relative to discharge nozzles of the containers. In the ON position, the actuator levers depress the discharge nozzles to cause simultaneous sprayed release of a sunless tanning product from the plurality of containers The tower is surrounded by a housing having vertically arranged nozzle openings aligned with the nozzles of the spray containers.

2 Claims, 2 Drawing Sheets

APPARATUS FOR SPRAY APPLICATION OF A SUNLESS TANNING PRODUCT

BACKGROUND OF THE INVENTION

1. Field of the Invention

The present invention is directed to an apparatus for releasing a sprayed discharge of a substance from one or more nozzles for application to the skin and, more particularly, to an apparatus for controlling release of spray discharge of a sunless tanning product from one or more aerosol containers for uniform application to the skin of a user's body.

2. Discussion of the Related Art

Automated sunless tanning spray systems are becoming extremely popular, particularly due to the danger of exposure to harmful ultraviolet light sources. Spray application of various sunless tanning products is available at commercial tanning salons. Such commercially available spray tanning systems for dispensing sunless tanning products use either hydraulic or air atomizing nozzles in various array configurations. The sunless tanning products are contained in large canisters or tanks and pumps are used to transfer the sunless tanning products from the tank through hoses and to the air atomizing nozzles, releasing a fine sprayed mist to achieve uniform application of the product to the skin. The spray tanning systems used at commercial spas and salons require expensive components such as pumps, cylinders and flow meters, making these systems considerably expensive. As a result, the cost of sunless tanning at commercial spas is rather expensive.

Various sunless tanning products are available for self-application at home. These products are provided in various forms including compact powder (e.g. application with a brush), foam, cream and liquid spray. Self application of a liquid spray sunless tanning product is difficult. Specifically, it is difficult to achieve uniform coverage of a liquid sprayed onto the skin, particularly from a pump style bottle dispenser. Release of liquid sunless tanning products has been found to be most effective when packaged with a propellant in a spray canister, such as an aerosol spray. Release with a propellant from a canister allows the liquid product to be discharged from a small atomizing nozzle to produce the desired fine disbursed mist that allows for uniform application to the skin. However, it is difficult to apply the sunless tanning product to the skin, even with the use of a aerosol propellant canister. In particular, it is difficult to hold the spray nozzle at the desired distance from the skin throughout the application process. Full body application is particularly difficult when attempting to hold the aerosol canister in one hand while reaching all areas of the body for uniform spray application. Thus, while spray application from an aerosol propellant canister has been found to be the most effective means for self application of various liquid sunless tanning products, it is difficult to achieve the desired uniform spray coverage to the skin, particularly when applying the product to the entire body.

Accordingly, there remains a need for a relatively inexpensive, yet highly effective apparatus for uniform spray application of a sunless tanning product to the skin. More particularly, there remains a need for an apparatus which is adapted to hold one or more canisters containing a sunless tanning product, wherein the product is released With the assistance of a propellant, such as aerosol, and wherein the apparatus is adapted to control actuation of the spray nozzles on the one or more canisters, thereby allowing the user to maintain a desired distance from the spray nozzles while turning the body to allow for uniform application.

SUMMARY OF THE INVENTION

The present invention is directed to an apparatus that releases a sunless tanning product from one or more containers for uniform spray application to the skin of the user. In a preferred embodiment, the apparatus is structured as a vertical tower and a plurality of containers are held in spaced vertical alignment so that each container is positioned in operative alignment below an actuator lever. A control knob is operatively linked to the actuator levers, whereupon operation of the control knob serves to move the actuator levers to simultaneously depress discharge nozzles on each of the containers, thereby causing sprayed release of the sunless tanning product with the assistance of a propellant, such as aerosol. In the preferred embodiment, the control knob is connected to a cam mechanism which, upon rotation thereof, serves to move a linkage to operate the levers relative to the discharge nozzles of the containers between an off position and an on position. The tower is surrounded by a housing having vertically arranged nozzle openings aligned with the nozzles of the spray containers. The control knob is accessible on the exterior of the housing. In another embodiment, the apparatus holds a single container of the sunless tanning product for spray application to the face.

BRIEF DESCRIPTION OF THE DRAWINGS

For a fuller understanding of the nature of the present invention, reference should be made to the following detailed description taken in conjunction with the accompanying drawings in which.

Like reference numerals refer to like parts throughout the several views of the drawings.

DETAILED DESCRIPTION OF THE PREFERRED EMBODIMENTS

Figure 1:
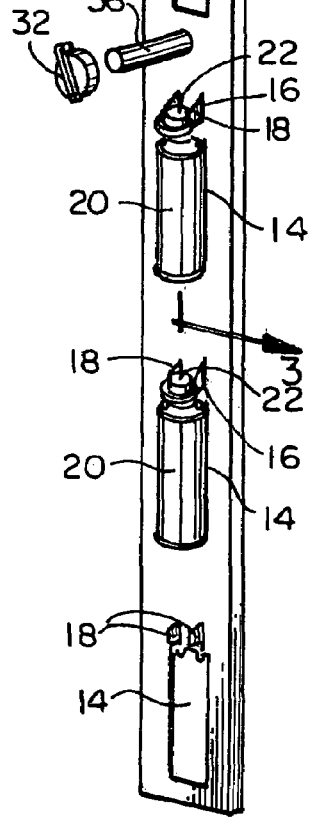
FIG. 1 is an isolated perspective view illustrating the frame structure and actuator assembly of the spray application apparatus of the present invention, wherein the frame structure an actuator assembly is adapted to hold a plurality of aerosol canisters, each containing a sunless tanning product therein, for simultaneous sprayed discharge from the plurality of containers.
Figure 2:
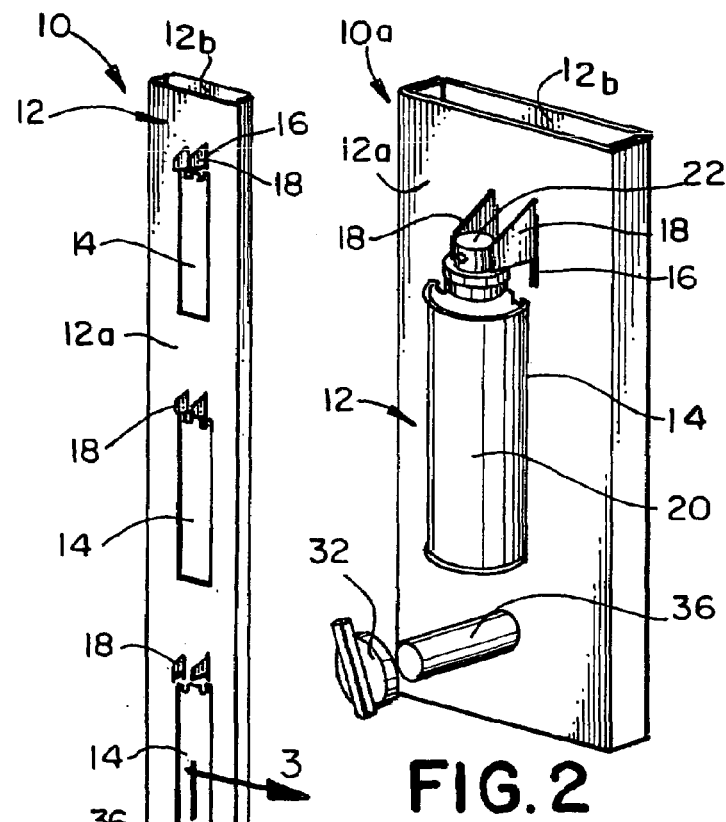
FIG. 2 is an isolated perspective view showing the frame structure and actuator assembly of the apparatus of the present invention, in accordance with a second embodiment thereof, wherein the frame structure and actuator assembly is adapted to hold a single aerosol canister for spray application of a sunless tanning product to the face.
Figure 4:
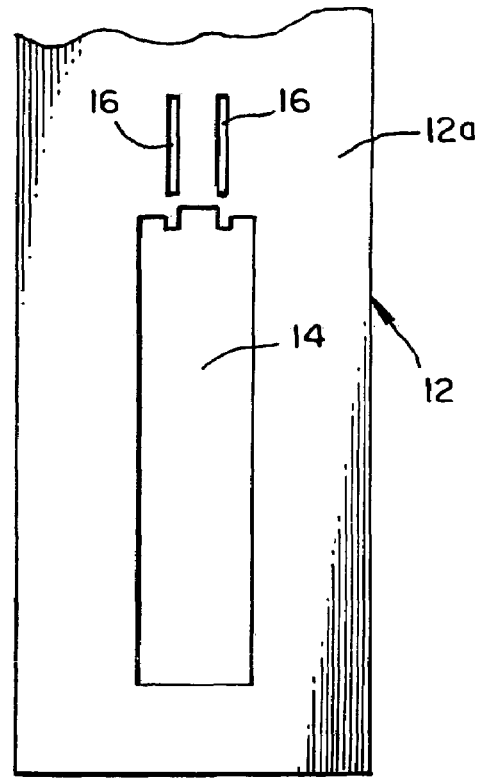
FIG. 4 is an isolated front elevational view showing a portion of the frame structure with an opening in the frame structure for holding a canister and a pair of parallel, spaced slots above the opening for accommodating passage of actuator levers in operable position above the spray nozzle of the canister.
Figure 3:
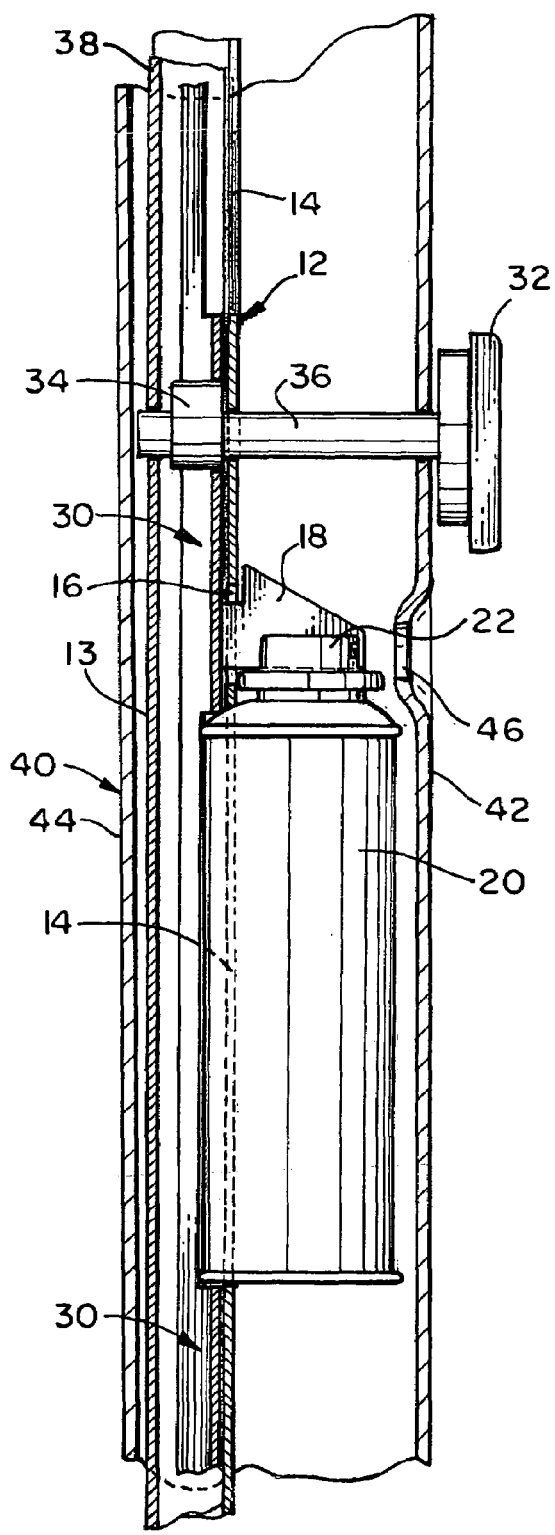
FIG. 3 is an isolated cross-sectional view taken along the plane indicated as 3-3 in FIG. 1 and showing an actuator assembly including a control knob, a cam and a linkage for moving an actuator lever in relation to a nozzle on the top of a canister held within the frame structure.

Referring initially to FIG. 1, a frame structure 12 of the apparatus 10 of the present invention is shown in accordance with the preferred embodiment, wherein the frame structure 12 is provided in a vertical, elongate configuration and includes a front frame member 12a and a rear frame member 12b. The front frame member 12a has a plurality of vertically spaced openings 14 for supporting a plurality of aerosol canisters therein. As seen in FIG. 4, each opening 14 in the frame structure is notched at the top portion for engaging the top end of the respective aerosol canister placed therein. Spaced slots 16 are provided above the opening 14 to accommodate passage of actuator levers 18 (see FIG. 1). The actuator levers 18 are positioned above the spray nozzle 22 of the aerosol canister 20. Operation of an actuator assembly 30 (see FIG. 3), by turning knob 32 to rotate cam 34 serves to move a linkage 38 that connects to the actuator levers 18. This moves the actuator levers 18 downwardly on the nozzles 22 of each of the canisters 20, causing the nozzles 22 to be depressed and, thereby simultaneously releasing a sprayed discharge of the sunless tanning product from the nozzles 22 of each canister 20. In an alternative embodiment an electronically powered solenoid is used to move the linkage 38, rather than the manually operated control knob. In this embodiment, a plunger on the solenoid is extended and retracted to move the linkage 38 and actuator levers 18.

Figure 5:
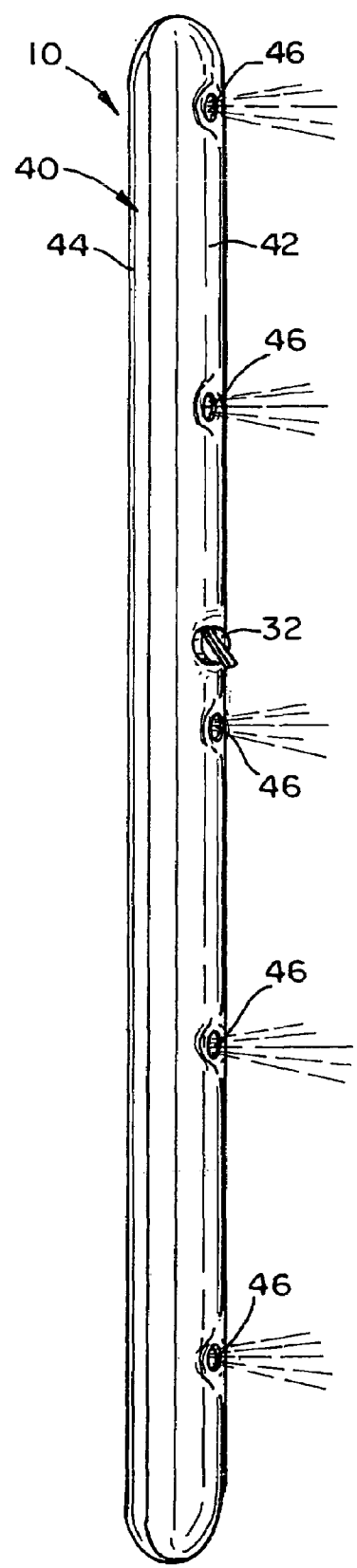
FIG. 5 is a perspective view showing the exterior housing of the apparatus of the present invention, with the sunless tanning product being sprayed from a plurality of vertically spaced discharge openings of the housing for uniform application to the entire body of the user.

The frame structure 12 and actuator assembly 30 are contained with a housing 40, as shown in FIG. 5. The housing 40 has an elongate configuration and includes a front half 42 and a rear half 44. The front half 42 is hinged to the rear half 44 to allow the front half 42 to swing open and closed. Opening the front half 42 provides access to the interior frame structure to allow replacement of the canisters 20 as well to permit as adjusts and repairs of the apparatus. The control knob 32 is exposed on an exterior of the housing. The housing 40 is provided with vertically spaced openings 46 aligned with the spray nozzles 22 of each of the plurality of aerosol canisters 20 contained therein, so that upon actuation of the apparatus, by rotating the control knob 32, the sunless tanning product is sprayed out from the openings 46 of the housing 40, in a disbursed, atomized mist for uniform application to the body of the user. The user, standing at a fixed distance from the vertical housing, simply turns in a slow, twirling motion, to allow the sprayed tanning product to be applied evenly to the skin surfaces of the body.

While the instant invention has been shown and described in accordance with a preferred and practical embodiment thereof, it is recognized that departures from the instant disclosure are contemplated within the spirit and scope of the present invention.

What is claimed is:

1. An apparatus for controlling release of a sunless tanning product from a plurality of containers each having a nozzle that is movable to operate a valve in order to cause sprayed release of the sunless tanning product from the nozzle, said apparatus comprising:
   a main frame structure for holding the plurality of containers;
   an actuator assembly for simultaneously operating the valve on each of the plurality of containers in order to control release of the sunless tanning product from the nozzle of each container, said actuator assembly including:
      at least one actuator lever movably disposed relative to said main frame and said container and in operative engagement with the nozzle on each of the plurality of containers, and said at least one actuator lever being movable between a first position wherein the valve of each of the plurality of containers is closed and the sprayed release of the sunless tanning product is stopped, and a second position wherein the nozzle of each of the plurality of containers is operatively moved to open the valve of each of the plurality of containers to cause the sprayed release of the sunless tanning product from the nozzle of each of the plurality of containers;
   a control operable between an OFF position and an ON position; and
   a linkage between said control and said at least one actuator lever, and said linkage being structured and disposed to move said at least one actuator lever between said first position and said second position upon operation of said control between said OFF position and said ON position, respectively; and,
   a housing surrounding said main frame structure and the plurality of containers, and said housing including an arrangement of discharge openings aligned with each of the nozzles of the plurality of containers for permitting passage of the simultaneous sprayed release of the sunless tanning product therethrough and exteriorly of said housing.

2. An apparatus for controlling release of a sunless tanning product from a plurality of containers each having a nozzle that is movable to operate a valve in order to cause simultaneous sprayed release of the sunless tanning product from the nozzle of each of the plurality of containers, said apparatus comprising:
   a main frame structure for holding the plurality of containers;
   an actuator assembly for simultaneously operating the valves on each of the plurality of containers in order to control simultaneous release of the sunless tanning product from the nozzle of the plurality of containers, said actuator assembly including:
      a plurality of actuator levers each movably disposed relative to a respective one of said plurality of containers and in operative engagement with the nozzle on the respective one of said plurality of containers, and said plurality of actuator levers being simultaneously movable between a first position wherein the valves on the plurality of containers remain closed and the sprayed release of the sunless tanning product from the nozzles of the plurality of containers is stopped, and a second position wherein the nozzles of the plurality of containers are operatively moved to open the valves of the plurality of containers and cause the simultaneous sprayed release of the sunless tanning product from the nozzles of the plurality of containers;
   a control operable between an OFF and an ON position;
   a linkage between said control and said plurality of actuator levers, and said linkage being structured and disposed to move the plurality of actuator levers between said first position and said second position upon operation of said control between said OFF position and said ON position, respectively; and
   a housing surrounding said main frame structure and the plurality of containers, and said housing including an arrangement of discharge openings aligned with each of the nozzles of the plurality of containers for permitting passage of the simultaneous sprayed release of the sunless tanning product therethrough and exteriorly of said housing.

* * * * *